United States Patent [19]
Barker

[11] Patent Number: 4,578,765
[45] Date of Patent: Mar. 25, 1986

[54] IMAGE COMPARISON SYSTEMS
[75] Inventor: John C. Barker, Oakington, England
[73] Assignee: Cambridge Instruments Limited, Cambridge, England
[21] Appl. No.: 543,037
[22] Filed: Oct. 18, 1983
[30] Foreign Application Priority Data
  Nov. 2, 1982 [GB] United Kingdom ................. 8231267
[51] Int. Cl.⁴ .............................................. G06K 9/00
[52] U.S. Cl. ...................................... 364/514; 382/54
[58] Field of Search ................. 371/67; 364/514, 513; 382/8, 34, 44, 54, 55; 356/237
[56] References Cited
U.S. PATENT DOCUMENTS

| 4,335,427 | 6/1982 | Hunt et al. | 382/54 |
| 4,345,312 | 8/1982 | Yasuye et al. | 382/8 |
| 4,403,114 | 9/1983 | Sakoe | 364/513 X |
| 4,445,185 | 4/1984 | Davis, Jr. et al. | 364/514 |
| 4,479,145 | 10/1984 | Azuma et al. | 382/8 X |
| 4,481,664 | 11/1984 | Linger et al. | 382/8 |
| 4,499,598 | 2/1985 | Chittineni | 382/54 |

Primary Examiner—Charles E. Atkinson
Attorney, Agent, or Firm—Leydig, Voit & Mayer, Ltd.

[57] ABSTRACT

The invention is for comparing a master image, stored by means of binary signals, with an image under test, which is stored by means of corresponding binary signals. Both sets of binary signals are fed out into an EXCLUSIVE OR gate. This will therefore produce output signals defining any differences between the image under test and the master image. In addition, however, the gate output binary signals due to any misalignment or digitization errors between the images stored in the two stores. To reduce or eliminate the latter, the master image is fed into an edge detector which produces binary signals representing a peripheral edge region or "frame" around the master image. This peripheral edge region is "dilated" (that is, the peripheral edge region is thickened to a predetermined extent). The signals representing the stored and dilated edge region are inverted and ANDed with the output of the EXCLUSIVE OR gate. Provided that the peripheral edge region has been sufficiently dilated, it will cancel out any binary signals produced by the EXCLUSIVE OR gate as a result of peripheral misalignment. The AND gate will therefore only output signals corresponding to the true errors between the two stored images.

7 Claims, 11 Drawing Figures

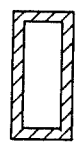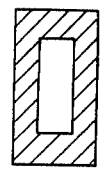
FIG.2A.   FIG.2B.   FIG.2C.
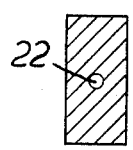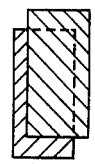
FIG.3A.   FIG.3B.   FIG.3C.
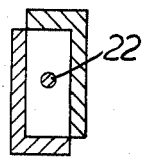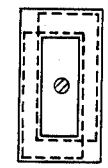
FIG.3D.   FIG.3E.   FIG.3F.
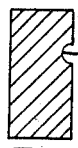
FIG.3G.

IMAGE COMPARISON SYSTEMS

BACKGROUND OF THE INVENTION

The invention relates to signal comparison systems. More specifically, it relates to signal comparison systems in which the signals represent visual images for instance. For example, embodiments of the invention may be used to facilitate the comparison of visual signals representing an image which has been produced by a manufacturing process with digital signals representing the desired form which the image should have, the comparison being carried out for the purpose of detecting errors in the image formed by the manufacturing process.

In carrying out such comparison processes, it is clearly important that the two images being compared, or the signals representing them, are accurately aligned. Any misalignment may be misinterpreted as errors in the image under test. Such misalignment can arise as a result of inevitable tolerances in the equipment producing the electrical signals from the manufactured image. Similar errors may result from the digitisation process used to produce the electrical signals representing the images being compared.

SUMMARY OF THE INVENTION

According to the invention, there is provided an image comparison system for carrying out a comparison between a first electrical signal set and a second electrical signal set which represent respective and nominally identical images, comprising means responsive to the first signal set for producing therefrom a third signal set representing the peripheral edge region of the image corresponding to the first signal set, signal processing means responsive to the third signal set for producing therefrom a modified third signal set representing a dilated version of the said peripheral edge region, first signal comparison means for comparing the first and second signal sets whereby to produce a difference signal set representing the signal differences therebetween, and second signal comparison means for comparing the difference signal set with the modified third signal set whereby to tend to remove from the difference signal set any difference signals corresponding to image differences lying within the said dilated peripheral edge region.

According to the invention, there is also provided a method of carrying out a comparison between a first electrical signal set and a second electrical signal set which represent respective and nominally identical images, comprising the steps of producing from the first signal set a third signal set representing the peripheral edge region of the image corresponding to the first signal set, producing from the third signal set a modified third signal set representing a dilated version of the said peripheral edge region, comparing the first and second signal sets whereby to produce a difference signal set representing the signal differences therebetween, and comparing the difference signal set with the modified third signal set whereby to tend to remove from the difference signal set any difference signals corresponding to image differences lying within the said dilated peripheral edge region.

DESCRIPTION OF THE DRAWINGS

An image comparison system embodying the invention will now be described, by way of example only, with reference to the accompanying diagrammatic drawings in which:

FIGS. 2, comprised of FIGS. 2A-2C, and 3, comprised of FIGS. 3A-3G, are diagrams illustrating the operation of the system.

DESCRIPTION OF PREFERRED EMBODIMENTS

Figure 1:
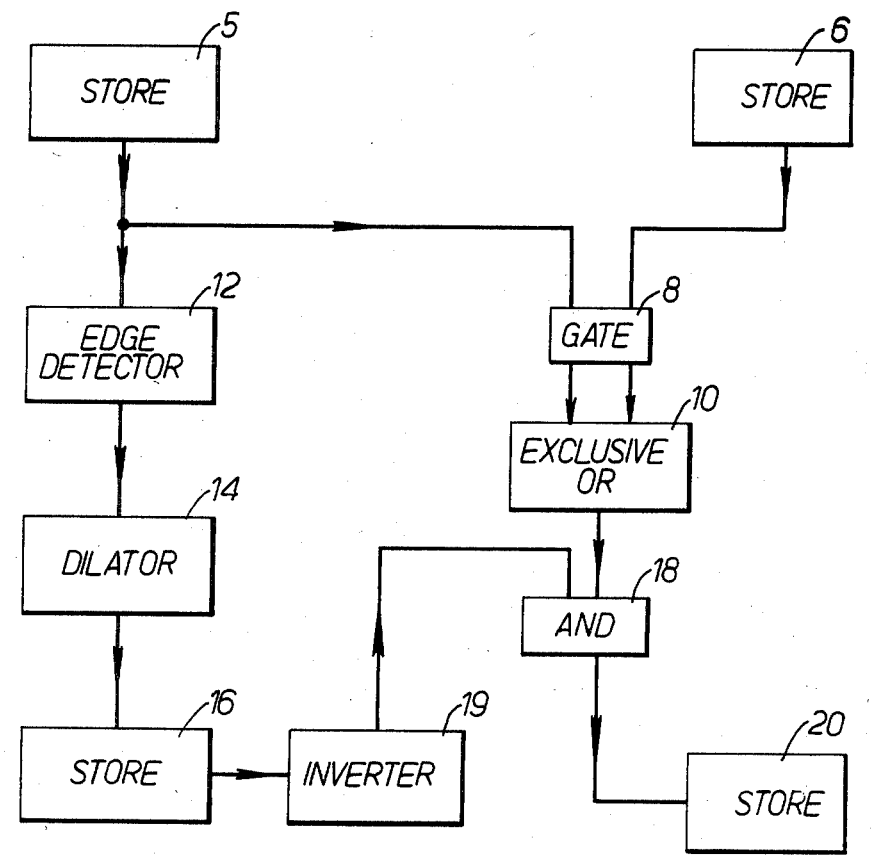
FIG. 1 is a block diagram of the system.

The system to be described is for comparing digital signals representing two images for the purposes of detecting differences between them.

By way of example, one set of signals may be digital signals representing the image produced from a reticle such as has been made for the purposes of producing integrated circuit wafers. Before each such reticle can be used, it must be checked against the master pattern for the reticle to ensure that there are no unacceptable errors—which would of course be transferred to the integrated circuit wafers.

The master pattern for the reticle may be held in a variety of ways. It might, for example, be held on a master reticle. However, in practice it is more likely to be held in the form of digital signals, these digital signals being used to control the manufacturing process from which the production reticles (that is, the reticles to be tested by the system being described) are produced.

As shown in FIG. 1, the digital signals representing the master pattern are stored in a master store 5. A store 6 stores digital signals defining the image of the reticle under test, these signals being produced from the reticle under test in any convenient way such as by scanning the reticle and reading off its pattern optically in the form of light and dark signals.

Thus, the stores 5 and 6 store digital signals, each digital signal representing a particular part of the respective image (the master image or the image under test), indicating whether that image part is light or dark.

The stores are connected through an output unit 8 to an EXCLUSIVE OR gate 10, and in this way, and in a manner to be described in more detail below, the value of each digital signal in the master store 5 is compared with the value of the corresponding digital signal in the store 6.

In addition, the digital signals in the store 5 are monitored by an edge detector 12. This detects the position and shape of the peripheral edge of the image represented by the digital signal in the store 5. In other words, it produces digital signals which define a peripheral edge region of the image in the store 5.

These digital signals are fed into a dilating unit 14 which modifies the digital signals so as to increase the width of the peripheral region which they represent, the width being increased to a predetermined extent, all in a manner to be explained in more detail below. The output of the dilating unit 14 is fed into a store 16. This thus stores digital signals representing a dilated peripheral edge region of the master image in the store 5.

An AND gate 18 is connected to receive the output from the EXCLUSIVE OR gate 10 through an inverter 19 and also to receive the output of the store 16, and the output of the AND gate 18 is fed into an output store 20.

The operation of the system will now be described with reference to FIGS. 2 and 3.

FIG. 2 shows the process carried out by the edge detector 12 and the dilator unit 14.

FIG. 2A shows the image which in this example is assumed to be represented by the digital signals in the master store 5. These digital signals are fed into the edge detector 12, and FIG. 2B shows the image which is represented by the digital signals produced by the edge detector 12 from those stored in the store 5. In other words, the edge detector 12 produces digital signals representing a "frame", being the peripheral edge region of the image shown in FIG. 2A. The edge detector 12 may comprise any suitable form of electrical circuit and, in particular, may comprise a circuit which detects transitions between digital signals representing a light area and digital signals representing a dark area. In this way, it is able to detect the digital signals defining the peripheral edge region of the image shown in FIG. 2A and these digital signals represent the image shown in FIG. 2B.

As already explained, these digital signals are fed into the dilator unit 14 (FIG. 1). This is arranged to dilate the image shown in FIG. 2B and represented by the digital signals produced by the edge detector 12. In other words, it responds to the digital signals output by the edge detector 12 so as to provide additional digital signals, stored in adjacent storage locations, so as effectively to dilate or thicken the peripheral edge regions represented by the digital signals produced by the edge detector 12. In this way, dilator unit 14 produces digital signals representing the image shown in FIG. 2C, and this is the image which is stored in the store 16.

FIG. 3 explains the operations carried out by the EXCLUSIVE OR and the AND gates 10 and 18.

FIG. 3A shows the image represented by the digital signals stored in the store 5, and is thus identical with FIG. 2A. FIG. 3B shows the image which is assumed to represented by the digital signals stored in store 6. As shown, this image is identical with that of FIG. 3A except that there is a "hole" 22 where (it is assumed) a fault in the manufacturing process has produced a small light area within the general dark area of the image.

The digital signals representing the images of FIGS. 3A and 3B are fed into the EXCLUSIVE OR gate 10 by the output unit 8 as explained in connected with FIG. 1, each digital signal from the store 5 being fed into the gate 10 at a time instant which is, at least nominally, the same as the time when the corresponding digital signal in the store 6 is fed into the gate 10.

However, and as explained above, because of misalignment and/or digitisation errors, the two images in the stores 5 and 6, even if identical in peripheral shape and size, may not exactly coincide. Therefore, when their signals are fed serially into the EXCLUSIVE OR gate 10, the effect may be as shown in FIG. 3C, where the two images are shown superimposed one upon the other but in exaggerated misalignment.

The EXCLUSIVE OR gate 10 will process the digital signals received so as to produce a binary "1" in the event of there being a difference between the two binary signals which are instantaneously present at the gate inputs, and a binary "0" when the digital signals there are the same. Therefore, the digital signals output from the exclusive or gate 10 will represent an image as shown in FIG. 3D, these digital signals representing the hole 22 and the areas of peripheral misalignment between the two images being compared. In other words, the output of the EXCLUSIVE OR gate 10 does not correctly represent the difference between the images being compared (that is the images in the stores 5 and 6) because the misalignment between the two compared images produces additional, spurious, signals as shown in FIG. 3D.

The signals represented by the image shown in FIG. 3D are fed into the AND gate 18, together with signals representing an inverted form of the image shown in FIG. 2C, the latter signals being fed through the inverter 19.

FIG. 3E shows diagrammatically the process carried by the AND gate 18. Effectively, the "frame" shown in FIG. 2C is being superimposed on the "frame" which is shown in FIG. 3D and which has been produced by the misalignment between these two images in the stores 5 and 6. To aid clarity, the cross-hatching has been omitted from FIG. 3E. Provided that the dilation carried out by the dilator unit 14 is sufficient to expand the "frame" of FIG. 2D to an extent which is great enough so that it fully covers the peripheral area shown in FIG. 3D, the latter will be cancelled (that is, no binary outputs will be produced by the gate 18). In this way, therefore, the only binary output produced by the gate 18 will be a binary output representing the hole 22, as shown in FIG. 3F and this binary output will be stored in the store 20. Therefore, the errors resulting from the misalignment between the images stored in the stores 5 and 6 have been elimianted.

It will be noted that the manner in which the misalignment errors have been cancelled in such that effectively the sensitivity of the system to errors due to misalignment has been reduced (so that these errors are completely eliminated in the best case and at least reduced in other cases) but without reducing the sensitivity to errors (the hole 22) which are nonperipheral. The misalignment error shown in FIG. 3C has been deliberately exaggerated. In practice, normally the misalignment error would be small and it would not be necessary for the dilator unit 14 (FIG. 1) to dilate the "frame" to any significant extent. In other words, the reduction in sensitivity for the peripheral comparison need not be so great as to prevent the detection of true peripheral errors. For example, if there is a "nick" or a "rat bite" type of error in the image stored in the store 6, as shown at 24 by way of example in FIG. 3G, this would normally still be detected.

The system described may be used with advantage in conjunction with the image inspection system disclosed in co-pending United Kingdon Patent Application No. 8231268 but is by no means limited to such an application.

What is claimed is:

1. An image comparison system for carrying out a comparison between a first electrical signal set and a second electrical signal set which represent respective and nominally identical images, comprising means responsive to the first signal set for producing therefrom a third signal set representing the peripheral edge region of the image corresponding to the first signal set, signal processing means responsive to the third signal set for producing therefrom a modified third signal set representing a dilated version of the said peripheral edge region, first signal comparison means for comparing the first and second signal sets whereby to produce a difference signal set representing the signal differences therebetween, and second signal comparison means for comparing the difference signal set with te modified third signal set whereby to tend to remove from the difference signal set any difference signals corresponding to image differences lying within the said dilated peripheral edge region.

2. A system according to claim 1, in which the said signal sets are sets of digital signals, each digital signal representing a respective portion of the image.

3. A system according to claim 2, comprising:
a store defining a plurality of storage locations, and
means responsive to the respective digital signals and connected to feed the digital signals into respective ones of the storage locations whose respective positions depend on the respective positions of the said image portions.

4. A system according to claim 1, in which the means for producing the third signal comprises two-dimensional edge detecting means.

5. A system according to claim 1, in which the first signal comparison means comprises EXCLUSIVE OR processing means responsive to the first and second signal sets.

6. A system according to claim 5, in which the second signal comparison means comprises means for performing a logical AND function on the combination of the output of the EXCLUSIVE OR means and the modified third signal set.

7. A method of carrying out a comparison between a first electrical signal set and a second electrical signal set which represent respective and nominally identical images, comprising the steps of
producing from the first signal set a third signal set representing the peripheral edge region of the image corresponding to the first signal set,
producing from the third signal set a modified third signal set representing a dilated version of the said peripheral edge region,
comparing the first and second signal sets whereby to produce a difference signal set representing the signal differences therebetween, and
comparing the difference signal set with the modified third signal set whereby to tend to remove from the difference signal set any difference signals corresponding to image differences lying within the said dilated peripheral edge region.

* * * * *